United States Patent [19]

Toon

[11] Patent Number: 4,536,199

[45] Date of Patent: Aug. 20, 1985

[54] GAS CHROMATOGRAPH FOR RESEPARATING A SAMPEL INTO PURE COMPONENTS

[75] Inventor: Michael B. Toon, De Soto, Tex.

[73] Assignee: Mobil Oil Corporation, New York, N.Y.

[21] Appl. No.: 568,462

[22] Filed: Jan. 5, 1984

[51] Int. Cl.³ .............................................. B01D 15/08
[52] U.S. Cl. ......................................... 55/67; 55/386; 422/70
[58] Field of Search ............................ 210/656-658, 210/198.2; 55/67, 386; 422/70

[56] References Cited

U.S. PATENT DOCUMENTS

| | | | |
|---|---|---|---|
| 3,264,801 | 8/1966 | Buhl et al. | 55/67 |
| 3,374,607 | 3/1968 | Fisher et al. | 55/67 |
| 3,698,869 | 10/1972 | Condon | 55/67 |
| 3,960,520 | 6/1976 | Allen | 55/67 |
| 4,180,389 | 12/1979 | Paul | 55/67 |

*Primary Examiner*—John Adee
*Attorney, Agent, or Firm*—Alexander J. McKillop; Michael G. Gilman; Charles J. Speciale

[57] ABSTRACT

A gas chromatograph includes valves for connecting the trapped components back to the column so that the trapped components can be reseparated to provide high purity of the trapped components.

10 Claims, 5 Drawing Figures

GAS CHROMATOGRAPH FOR RESEPARATING A SAMPEL INTO PURE COMPONENTS

BACKGROUND OF THE INVENTION

This invention relates to gas chromatographs and more particularly, to a gas chromatograph and a method of operating it to reseparate trapped components.

Gas chromatographs are extensively used to separate samples into their components. For example, gas chromatographs are used in geochemical analysis of the quantitative distribution of hydrocarbons in crude oils. A crude oil sample is separated by gas chromatography into its components. Typically, each of these components is then burned to $CO_2$ and the combustion products are analyzed in a mass spectrometer to determine the ratios of the carbon isotopes in each sample. This technique is described in "CORRELATION OF NATURAL GAS BY USE OF CARBON ISOTOPIC DISTRIBUTION BETWEEN HYDROCARBON COMPONENTS" by Alan T. James, American Association of Petroleum Geologists Bulletin, V. 67, No. 7(July 1983). A gas chromatograph-combustion system for performing such analysis is shown in FIG. 2, page 10, of "HYDROUS PYROLYSIS AS A THERMAL ALTERATION SIMULATION TECHNIQUE", Research Report No. 125, February 1983, Energy Resources Group Exploration and Production Research Technology Center, Cities Service Company, Tulsa, Okla.

In such analyses it is extremely important to separate a sample into high purity components. The isotopic concentration of a separated component may be drastically altered if another component is present in even minute amounts. For example when a separation is made between $IsoC_4$ and normal $C_4$, even if the amount of normal $C_4$ contaminating the $IsoC_4$ cut is less than 1%, this will have a drastic effect on the measurement of the isotope concentrations of the $IsoC_4$ component.

It is an object of the present invention to provide a gas chromatograph which produces extremely pure components of a sample.

SUMMARY OF THE INVENTION

In accordance with the present invention, a gas chromatograph has valve means for selectively connecting an external sample source to the chromatographic column and detector, or alternatively, to connect a component which has already been trapped to the chromatographic column and detector. In this way, trapped components can be reseparated to ensure the isotopic purity of the trapped component. The component can be reseparated as many times as necessary to ensure purity.

The foregoing and other objects, features and advantages of the invention will be better understood from the following more detailed description and appended claims.

SHORT DESCRIPTION OF THE DRAWINGS

DESCRIPTION OF THE PREFERRED EMBODIMENT

Figure 1:
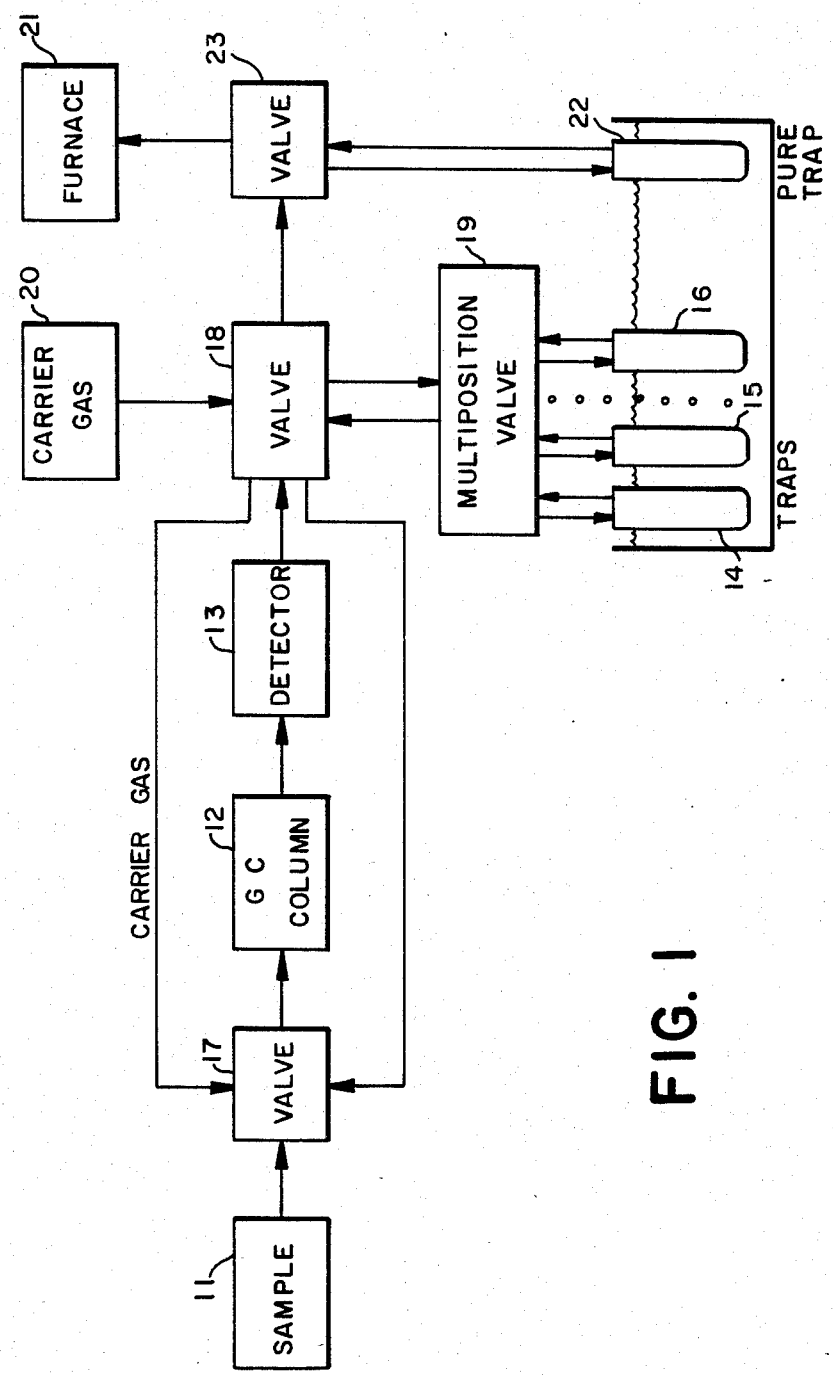
FIG. 1 is block diagram depicting the gas chromatograph of the present invention.

Referring to FIG. 1, the gas chromatograph separates a sample from source 11 into its components. A chromatographic column 12 separates the sample into components, the properties of which are measured by detector 13, commonly a thermal conductivity detector.

In response to peaks in thermal conductivity, the components are connected to one or another of the traps 14–16 and others, which trap a component from the carrier gas. In accordance with the present invention, the components in the traps 14–16 can be connected through valve means to the column 12 so that the trapped components can be reseparated.

A first valve 17 selectively connects a sample from an external source to the chromatographic column 12 or, alternatively, supplies a component in one of the traps 14–16 to the chromatographic column 12. A second valve 18 selectively connects a component in one of the traps through valve 17 and gas chromatographic column 12 to detector 13, or, alternatively, valve 18 connects a component passing through detector 13 to one of the traps 14–16. A third valve 19 has multiple positions which access each of the traps 14–16.

A source of carrier gas 20 is used to transport the sample through the column and detector to the traps and is used to flush trapped components from the traps 14–16 back through the column 12 and detector 13. Valve 18 selectively supplies the carrier gas to the valve 17 or to the traps for flushing trapped components.

A furnace 21 burns the trapped components to produce combustion products for analysis. For example, in geochemical analysis, the components of methane are burned to $CO_2$ for mass spectrometry measurement of the carbon isotopes.

A pure trap 22 may be used to collect a component which has been reseparated to ensure purity. A fourth valve 23 selectively connects a component in one of the traps 14–16 to the furnace 21, or to the pure trap 22.

Figure 2A:
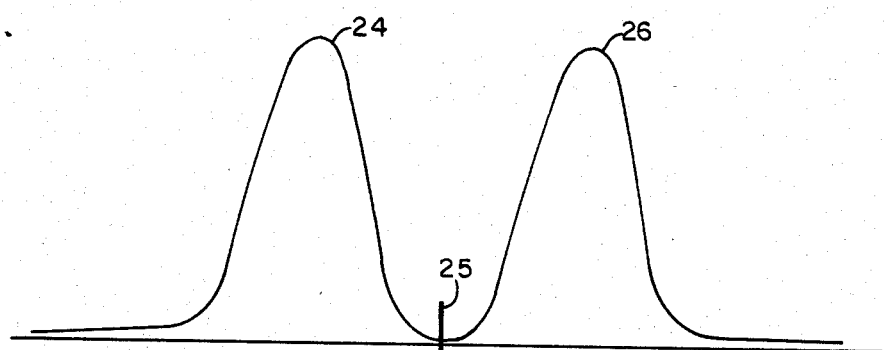
FIGS. 2A-2C depict thermal conductivity peaks produced by the detector.
Figure 2B:
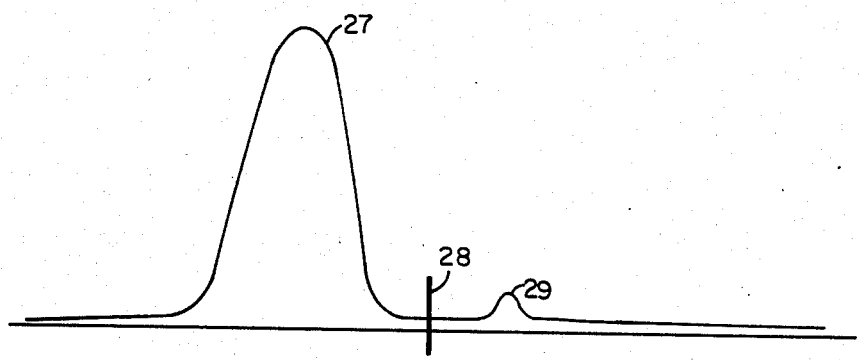
Figure 2C:
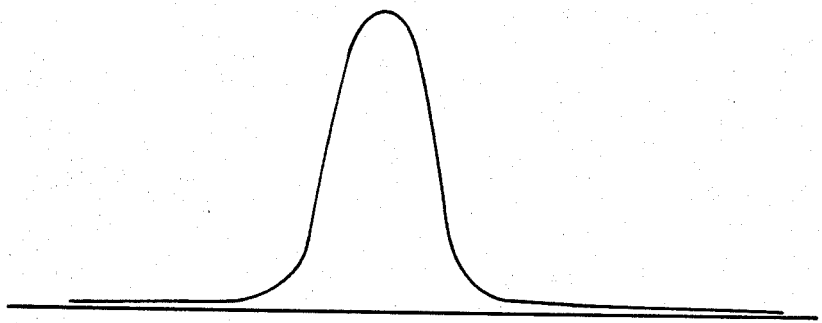

FIGS. 2A-2C depict thermal conductivity peaks produced during the separation of a methane sample into $IsoC_4$ and normal $C_4$. FIG. 2A depicts the first pass through the chromatographic column. The peak 24 indicates the detection of $IsoC_4$ from the column. This is supplied to one of the traps, for example, trap 14. At the point marked 25, multiple position valve 19 is switched so thereafter the component emanating from column 12 is supplied to another trap, for example 15. This is the normal $C_4$ component and it is detected and produces the peak 26 in the thermal conductivity curve. However, it has been found that even the most precise gas chromatographs cannot separate components with the purity required for some isotopic analyses. When the $IsoC_4$ component is reseparated by the chromatograph of the present invention, the thermal conductivity curve of FIG. 2B is typical. The peak 27 indicates the $IsoC_4$ component which is supplied to one trap. A switch in traps is made at the time 28. It will be noted that a much smaller peak 29 is produced indicating that a small amount of normal $C_4$ was present in the trapped $IsoC_4$ component. Even if this amount is less than 1%, the isotopic composition of the normal $C_4$ component may be drastically altered. Ideally, the component will reseparated until a thermal detection pattern shown in FIG. 2C is produced indicating high purity $IsoC_4$.

Figure 3:
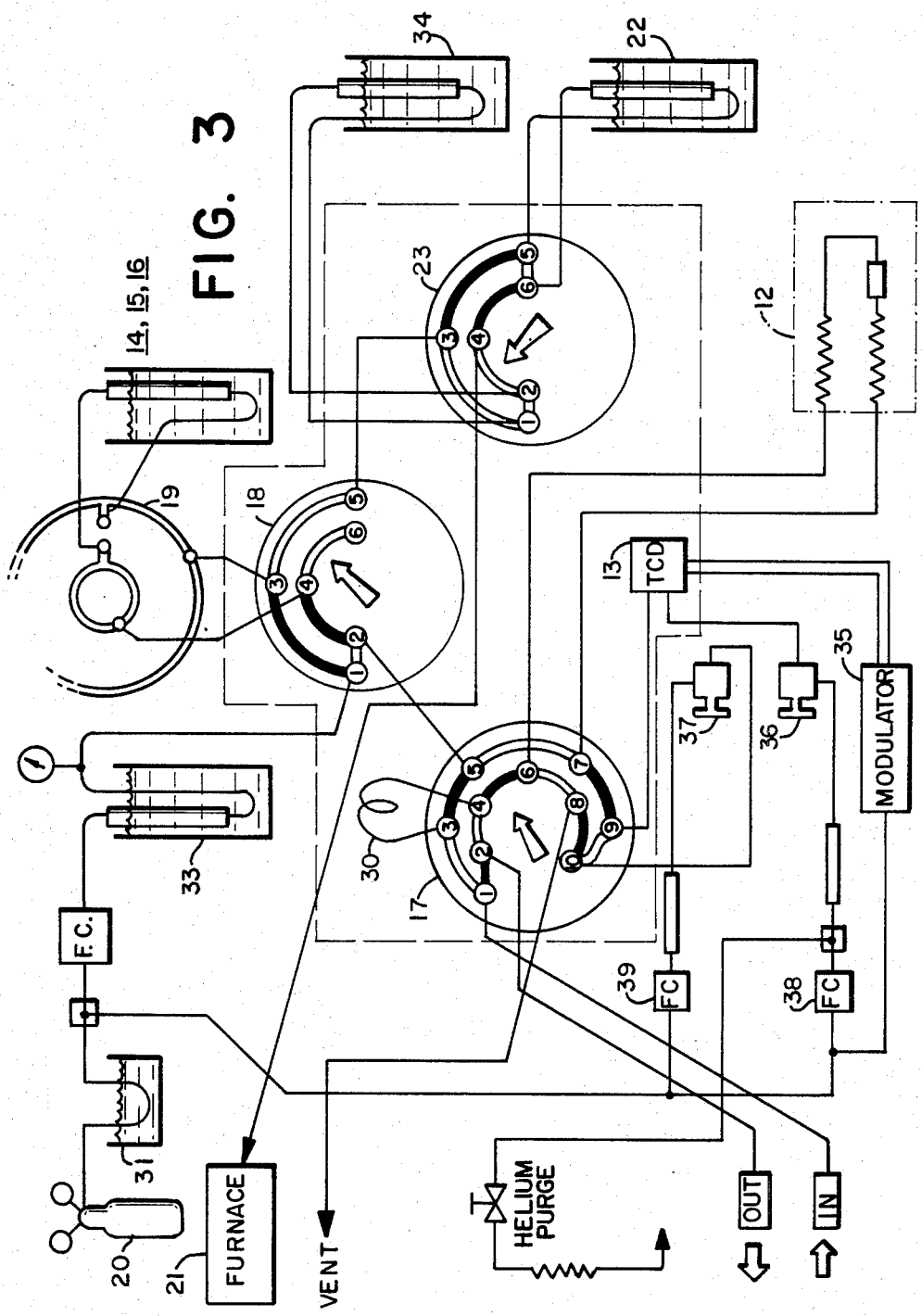
FIG. 3 is a more detailed drawing of the flow path of the gas chromatograph of the present invention.

The flow diagram of the gas chromatograph of the present invention is shown in more detail in FIG. 3.

Valves 17, 18, and 23 are multiple port sampling/switching valves. The convention used to depict them is that the numbered ports of each valve are connected by the hollow lines when the valve is in one position, and the ports are connected by the solid lines when the valve is in its other condition. For example, valve 17 is shown in its counterclockwise position, with port 1 connected to port 3, port 5 connected to port 7, port 6 connected to port 8, and port 9 connected to port 10. In its clockwise position, port 1 is connected to port 2, port 3 to port 5, port 4 to port 6, port 7 to port 9 and port 8 to port 10. Valve 18 is shown in its clockwise position, and valve 23 is shown in its counterclockwise position.

A sample from an external source passes through ports 1 and 3 of valve 17, through sample loop 30, through ports 4 and 2 of valve 17 and to vent. After a sample is loaded, valve 17 is switched to its clockwise position. Carrier gas from source 20, primary trap 31, and carrier trap 32 is supplied through ports 1 and 2 of valve 18, through ports 5 and 3 of valve 17, through sample loop 30, and ports 4 and 6 of valve 17, to transfer the sample to the column 12 and thence through ports 7 and 9 of valve 17 to the thermal conductivity detector 13. As the sample is separated into its components, the components are supplied through ports 6 and 4 of valve 18 to the distributor of multi-position valve 19 and from there to one of the traps 14, 15 . . . 16. As the separation is made, multiple position valve 19 is moved to supply the components to other traps.

In order to reseparate the trapped components, valve 18 is moved to its counterclockwise position. Carrier gas from carrier trap 33 passes through ports 1 and 3 of valve 18, through valve 19 to the selected trap which is flushed by the carrier gas. The trapped component is carried through the distributor of valve 19, through ports 4 and 2 of valve 18, through ports 5 and 3 of valve 17, through the sample loop 30, through ports 4 and 6 of valve 17, through column 12, through ports 7 and 9 of valve 17 to the thermal conductivity detector 13. Thereafter, another separation is made in the same manner as previously described. The steps of separating, detecting and directing the components to a different trap are repeated as many times as necessary to obtain a pure separation.

The component from one of the traps 14, 15 . . . 16 is connected through ports 3 and 1 of valve 23 to the fixed restrictor 34 when valve 23 is in its counterclockwise position, as shown. This fixed restrictor conditions the component to the proper temperature and pressure for burning in furnace 21 without causing a pressure fluctuation which would cause a baseline upset in the detector. From the fixed restrictor 34, the component passes through ports 2 and 4 of valve 23 to the furnace 21.

When the valve 23 is moved to its clockwise position, a component from one of the traps, 14, 15 . . . 16 is connected through ports 3 and 5 of valve 23 to the pure trap 22. The trapped pure component remains in trap 22 and the carrier gas passes through ports 6 and 4 of valve 23 to the furnace 21.

In an actual embodiment of the invention, valves 17, 18 and 23 are helically driven, air-actuated, multiple port switching valves supplied by Valvco Corporation, Austin, Tex. These valves are installed in a heated valve enclosure. The valving was installed on a Hewlett-Packard 5880 gas chromatograph which includes a modulator 35 and flow control valves 36–39 for alternately supplying carrier gas and sample to thermal conductivity detector 13.

While a particular embodiment of the invention has been shown and described, various modifications are within the true spirit and scope of the invention.

What is claimed is:

1. A gas chromatograph for separating the components of a sample comprising:
   a chromatographic column for separating said sample into its components;
   a detector for measuring the properties of said components;
   means for holding said sample and connecting it to said detector;
   a plurality of traps for trapping the components of said sample;
   a first valve selectively connecting said means for holding said sample to an external source of sample or to a component trapped in one of said traps and;
   a second valve for selectively connecting said traps to supply a component trapped in one of said traps to said detector or to supply a component passing through said detector to one of said traps so that the trapped components can be reseparated.

2. The gas chromatograph recited in claim 1 further comprising:
   a third valve connected between said second valve and said traps for connecting components passing through said second valve to one of said traps.

3. The gas chromatograph recited to claim 1 wherein said means for holding said sample further comprises:
   a sample loop for holding said sample and connecting it to said detector;
   and wherein said first valve selectively connects said sample loop to an external source of sample or a component trapped in one of said traps.

4. The gas chromatograph recited in claim 3 further comprising:
   a source of carrier gas connected by said second valve to said first valve to flush a sample from said sample loop to said detector;
   said second valve selectively connecting said source of carrier gas to flush a trapped component from one of said traps to said sample loop.

5. The gas chromatograph recited in claim 1 further comprising:
   a furnace for burning the trapped components to produce combustion products for analysis.

6. The gas chromatograph recited in claim 5 further comprising:
   a pure trap, the reseparated components being supplied to said pure trap.

7. The gas chromatograph recited in claim 6 further comprising:
   a fourth valve selectively connecting a component trapped in one of said traps to said furnace or to said pure trap.

8. The gas chromatograph recited in claim 7 further comprising:
   a fixed restrictor for conditioning said components for combustion, said fourth valve selectively connecting said fixed restrictor between said third valve and said furnace.

9. The apparatus recited in claim 1 wherein said detector is a thermal conductivity detector.

10. The method of operating a gas chromatograph comprising:
    separating a sample into its components in a chromatographic column;

detecting the thermal conductivity of the separated components;

operating valves which connect each of said components to a different trap in response to indicated peaks in said thermal conductivity;

operating a valve which selectively connects a means for holding said sample to an external source of sample or to a component trapped in one of said traps;

thereafter connecting said means for holding said sample loop to said detector:

and repeating the steps of separating, detecting and operating valves which connect each of said components to a different trap.

* * * * *